(12) United States Patent
Blin

(10) Patent No.: US 9,675,362 B2
(45) Date of Patent: Jun. 13, 2017

(54) DEVICE FOR HAEMOSTATIC CONTROL OF A BLOOD FLOW

(75) Inventor: Dominique Blin, La Tronche (FR)

(73) Assignee: UNIVERSITE JOSEPH FOURIER, Grenoble (FR)

( * ) Notice: Subject to any disclaimer, the term of this patent is extended or adjusted under 35 U.S.C. 154(b) by 756 days.

(21) Appl. No.: 12/866,496

(22) PCT Filed: Feb. 9, 2009

(86) PCT No.: PCT/FR2009/050198
§ 371 (c)(1),
(2), (4) Date: Nov. 15, 2010

(87) PCT Pub. No.: WO2009/101348
PCT Pub. Date: Aug. 20, 2009

(65) Prior Publication Data
US 2011/0066178 A1    Mar. 17, 2011

(30) Foreign Application Priority Data

Feb. 8, 2008 (FR) ..................................... 08 00676

(51) Int. Cl.
*A61M 1/00* (2006.01)
*A61B 17/132* (2006.01)
(Continued)

(52) U.S. Cl.
CPC ....... *A61B 17/1325* (2013.01); *A61M 1/0031* (2013.01); *A61M 1/0088* (2013.01);
(Continued)

(58) Field of Classification Search
CPC ............ A61B 17/442; A61B 2017/308; A61B 2017/306; A61B 17/1325; A61B 17/08;
(Continued)

(56) References Cited

U.S. PATENT DOCUMENTS 3,202,152 A  *  8/1965  Wood et al. ................... 606/123
4,633,865 A  *  1/1987  Hengstberger et al. ...... 606/201
(Continued)

FOREIGN PATENT DOCUMENTS

WO   WO 2006/012992   *   2/2006   ............. A61M 1/00
WO      2006/048246        5/2006
(Continued)

OTHER PUBLICATIONS

International Search Report dated Sep. 14, 2009, from corresponding PCT application.
(Continued)

*Primary Examiner* — Christopher L Templeton
(74) *Attorney, Agent, or Firm* — Young & Thompson

(57) ABSTRACT

Device for haemostatic control of a blood flow, comprising a suction cup which provides leaktight coverage and is able to surround and be applied tightly to a tissue area (2) that is to be treated, said tissue area (2) being the site of a haemorrhage or of a blood flow that is to be controlled, this suction cup (3) coming into contact with the periphery of the tissue area and delimiting an internal volume (8) which is connected in a leaktight manner, by a catheter or a similar connecting tube (7), to an external aspiration element that establishes a vacuum, so as to create an underpressure of defined value within this volume between the suction cup and the tissue area, the suction cup (3) having the general shape of a dome (4), of which the base (5) supports an inner bearing element (11) that can be arranged opposite the tissue area (2) under the suction cup (3). The invention lies in the inner bearing element being formed by a solid obturator (11) or an open grill (13).

13 Claims, 2 Drawing Sheets

(51) Int. Cl.
*A61M 1/08* (2006.01)
*A61B 17/30* (2006.01)
*A61F 13/00* (2006.01)

(52) U.S. Cl.
CPC ......... *A61M 1/08* (2013.01); *A61B 2017/306* (2013.01); *A61B 2017/308* (2013.01); *A61F 2013/00174* (2013.01); *A61M 1/00* (2013.01); *A61M 1/0023* (2013.01); *A61M 2205/3334* (2013.01)

(58) Field of Classification Search
CPC .......... A61B 2017/081; A61M 1/0088; A61M 1/0023; A61M 1/008; A61M 1/009; A61M 1/0058; A61M 27/00; A61M 1/0031; A61M 1/08; A61M 1/0064; A61M 1/0066; A61M 1/0074; A61M 1/0068; A61F 2013/00174; A61F 2013/0028; A61F 2013/00468; A61F 2013/00463; A61F 2013/00544; A61F 13/00068; A61F 13/0216; A61F 13/00
USPC ........ 606/213, 215, 216, 123, 122; 604/313–316, 541, 543, 317, 328, 337, 604/27, 35, 48, 73, 74, 93.01, 128, 264, 604/540, 268
See application file for complete search history.

(56) References Cited

U.S. PATENT DOCUMENTS

| | | | |
|---|---|---|---|
| 4,730,617 A * | 3/1988 | King | 606/123 |
| 5,019,086 A * | 5/1991 | Neward | 606/123 |
| 5,224,947 A * | 7/1993 | Cooper et al. | 606/123 |
| 5,281,229 A * | 1/1994 | Neward | 606/123 |
| 5,645,081 A | 7/1997 | Argenta et al. | |
| 5,693,058 A * | 12/1997 | Cavanagh et al. | 606/123 |
| 5,713,909 A * | 2/1998 | Lindsay | 606/123 |
| 5,810,840 A * | 9/1998 | Lindsay | 606/123 |
| 5,906,607 A * | 5/1999 | Taylor et al. | 606/1 |
| 5,935,136 A * | 8/1999 | Hulse et al. | 606/123 |
| 6,179,845 B1 * | 1/2001 | Peters et al. | 606/123 |
| 6,558,344 B2 * | 5/2003 | McKinnon et al. | 604/35 |
| 6,626,891 B2 * | 9/2003 | Ohmstede | 604/543 |
| 6,723,105 B1 * | 4/2004 | Hulse et al. | 606/123 |
| 7,198,046 B1 | 4/2007 | Argenta et al. | |
| 7,216,651 B2 | 5/2007 | Argenta et al. | |
| 7,361,184 B2 * | 4/2008 | Joshi | 606/213 |
| 7,381,859 B2 * | 6/2008 | Hunt et al. | 602/46 |
| 7,540,860 B2 * | 6/2009 | Stamler | 604/268 |
| 7,569,742 B2 * | 8/2009 | Haggstrom et al. | 602/53 |
| 7,615,036 B2 | 11/2009 | Joshi et al. | |
| 7,935,094 B2 * | 5/2011 | Lonky | 604/320 |
| 2004/0243073 A1 | 12/2004 | Lockwood et al. | |
| 2005/0203334 A1 * | 9/2005 | Lonky et al. | 600/37 |
| 2007/0055209 A1 * | 3/2007 | Patel et al. | 604/315 |
| 2007/0198027 A1 * | 8/2007 | Morch | 606/123 |
| 2008/0004559 A1 | 1/2008 | Riesinger | |
| 2008/0009812 A1 | 1/2008 | Riesinger | |
| 2008/0051828 A1 * | 2/2008 | Sample et al. | 606/213 |
| 2008/0065001 A1 * | 3/2008 | DiNucci et al. | 604/19 |
| 2008/0125792 A1 * | 5/2008 | Giardina et al. | 606/123 |
| 2010/0063464 A1 | 3/2010 | Meyer et al. | |

FOREIGN PATENT DOCUMENTS

| | | | |
|---|---|---|---|
| WO | 2006/105892 | 10/2006 | |
| WO | WO 2007/068477 * | 6/2007 | A61F 13/02 |
| WO | 2007/133644 | 11/2007 | |
| WO | 2008/141228 | 11/2008 | |

OTHER PUBLICATIONS

French Search Report dated Sep. 29, 2008, from corresponding French application.

* cited by examiner

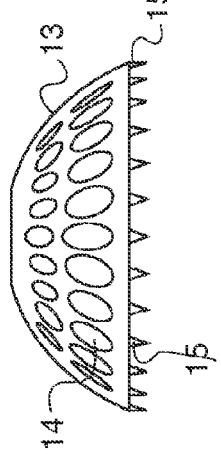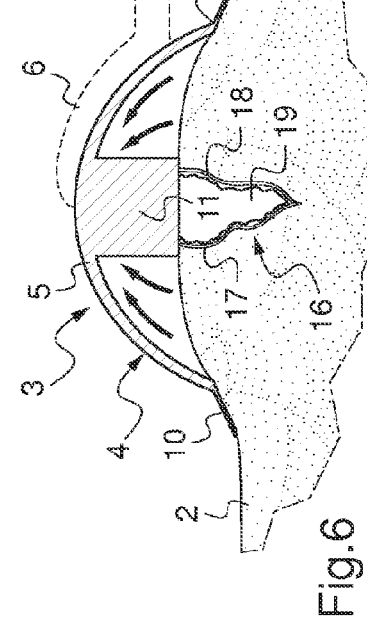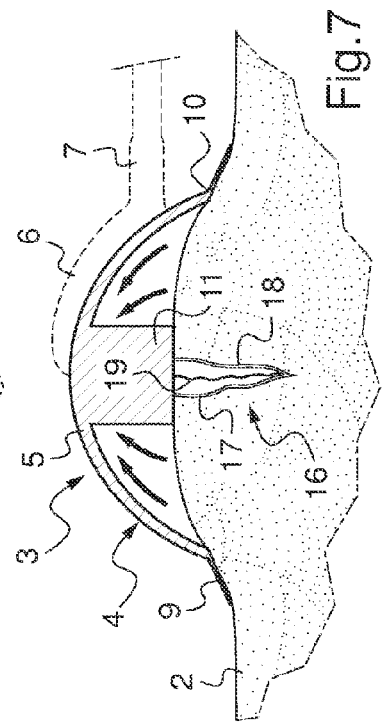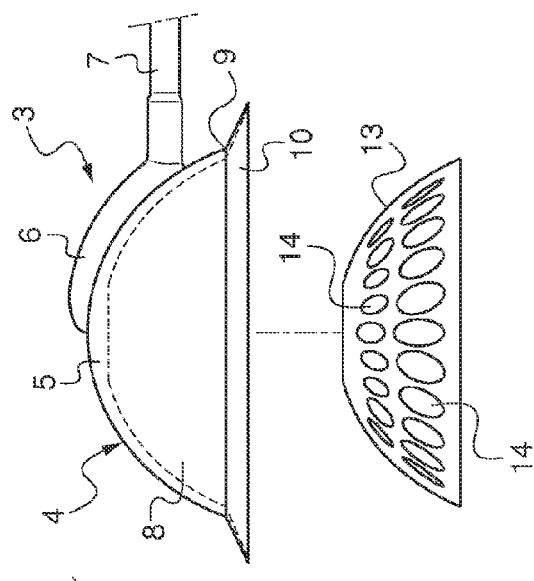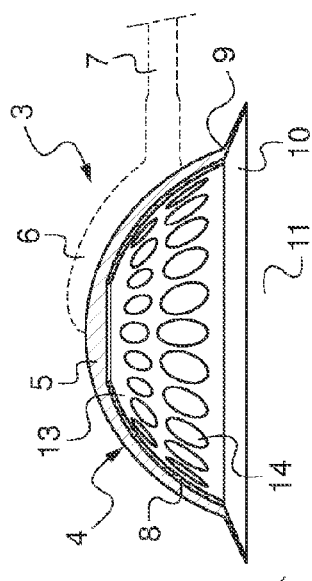

DEVICE FOR HAEMOSTATIC CONTROL OF A BLOOD FLOW

This invention relates to a device for the haemostatic control of bleeding, such as may happen, whether during a surgical operation on a delicate organ, notably the heart, or in the case of an accidental vascular lesion.

During a surgical operation, and all the more in the case of a serious accidental injury, haemostasis for important bleeding episodes generally raises four kinds of problems.

Firstly, the wound may be difficult to observe in the case of an important bleeding; it may also be difficult to suture considering the delicacy of the damaged tissues.

Moreover it is not normally possible to control the wound by clamping; finally, it may be situated in a dangerous area requiring very special surgery skills.

Thus these haemorrhages may be such that they disrupt the operation area unless under control and limited, or even totally stopped, thus requiring an immediate haemostasis by way of usual compression or electrocoagulation operations, or else with an operation wherewith the two ends of the wound are pinched in order to help it heal more rapidly, wherein these operations may be carried out cumulatively one after the other or separately according to circumstances.

Now in both cases the haemorrhage may however continue during a variable length of time, and with a variable bleeding volume.

Moreover, as already mentioned hereabove, in some cases this bleeding takes place in areas which are inaccessible or difficult to access by the surgeon, which makes the wound harder to observe, or in places where the tissues are very delicate and their repair a difficult task.

In order to overcome these difficulties and to allow under the best conditions a haemostasis of the damaged tissue where the bleeding takes place, it has already been suggested to implement a method which reveals often satisfactory, above all if the wound is comparatively superficial.

A method has notably already been suggested, in order to treat such superficial wounds, whether infected or not, whereby vertically from the wound or in contact with the bared tissue an aspirative drainage is implemented, thus triggering an evacuation of infected dead particles, together with some tissue migration favouring haemostasis, or even, in the case of slight injuries, a possible healing of the wound.

However, the suggested embodiments, of which US Pat. Nos. 5,645,081, 7,198,046, 7,216,651 or 2004/0243073, present several variants, are best adapted to wounds which are comparatively superficial, with more benign tissue lesions, owing to the use of a bell-shaped device or of a tight bandage which is applied onto the circumference of the injured area in order to create a closed space above it, and linked to an outside vacuum source, and if need be via exudate decanting or impurity filtering means, and this for a notable length of time. One may also refer to the embodiment as described on the Medtronic Website.

The aim of the invention is to improve the known vacuum extraction technique of an area in a tissue where an haemorrhage takes place, notably when bleeding is important and relates to a delicate internal organ, by way of a device which allows one to carry out and control this extraction in order to obtain an efficient, quick and safe haemostasis, which may be maintained as long as necessary so as to complete the surgical operation or the treatment of the wound, under optimal conditions, notably visual, of said wound, while practically eliminating the bleeding episode which might disturb it.

To this end said device includes a water-tight collecting suction cup, which may surround and tightly contact an area of the tissue to be treated, and where a haemorrhage or bleeding to be controlled takes place, wherein this suction cup comes into contact with the circumference of the tissue area and defines an inner volume which is tightly linked through a catheter or similar linking tube to an external suction and vacuum device, thus creating in said volume, between the suction cup and the tissue area, a depression having a determined value, wherein the suction cup has a general shape of a dome, with the bottom bearing at least an internal support device, which may come face to face with the tissue area under the suction cup.

Owing to these arrangements, which are known by themselves, the wound heals up due to tissue migration as a consequence of the depression which is thus created, wherein the internal support device essentially maintains the tissue in place at the base of the dome.

According to the invention, and in a first embodiment, the internal support device is made up by a solid obturator, which has been made integral with the bottom of the suction cup.

In a preferred embodiment, the dome of the suction cup has a hemispheric profile around an axis of rotation in the direction of which is placed the obturator, which is essentially in the center of the dome.

Also preferably the obturator has the shape of a straight cylinder having the same axis as the axis of rotation of the dome.

The height of the obturator is essentially greater than that of the hemispheric profile dome, in order to exert a compression force onto the tissue area when the edge of said dome, as opposed to its bottom, is applied onto the area. In some cases the height of the obturator may be slightly lower than that of the dome, in order to make it easier to position the cup against the tissue area.

The obturator includes, at the bottom of the dome, a water-tight connecting device with the linking tube, which itself is linked with the external device for creating a vacuum, and at least an opening which communicates with the inner volume of the dome for sucking up the air which is contained in said volume.

As the case may be, the dome and the obturator may be manufactured integrally to form a single-piece unit; the dome and the obturator may also be manufactured separately, and later glued together at the bottom of the dome.

Furthermore, and as a rule, the obturator diameter is essentially one half of the dome diameter, as seen vertically directly above its edge as applied against the tissue area.

In another embodiment of the invention, the inner support device is made up by a perforated grid with a plurality of through holes for freely letting in the air into the dome volume before it is discharged into the linking tube through the external vacuum-creating device.

Preferably the through holes in the grid may or may not be identical, circular, or have a different profile, and in some cases they may be regularly distributed over its whole surface.

The circumference of the grid may also include slightly projecting embossed contact teeth in order to slightly penetrate into the superficial layer of the tissue area when the dome is applied onto said area.

According to another advantageous feature, and whatever embodiment is chosen, the edge of the dome, as opposed to its bottom, includes a circular plane support flange in contact with the tissue area which it surrounds. Advantageously this flange has an essentially conical profile on the flange axis.

The dome may be flexible and be made of a silicone resin or similar material which is biocompatible with the tissue area to be treated. However it may be made of a rigid hardened epoxy resin type material, with an adhesive silicone protecting cover.

According to the size of the tissue area to be treated, and notably the kind of haemorrhage or bleeding to be controlled, the dome diameter directly above its edge as applied against this area may be variable from one embodiment to another, and notably be between 5-60 mm, preferably and on average about 50 mm. In the same manner, and as the case may be, the height of the dome may vary between 10-30 mm.

According to yet another feature, the external means for creating a vacuum is made up of a pump or a Redon type suction bowl, and the depression which is created may vary between significant limits, but is usually between 500-700 mm Hg.

Yet additional features of a haemostatic control device according to the invention will appear through the following specification of various embodiments given as indications and not as limitations, with reference to appended drawings, wherein:

FIG. 4 is an exploded view, in elevation, of a variant of the suction cup from FIGS. 2 and 3, wherein the inner support device is made up by a perforated grid.

FIG. 5 illustrates an alteration of the grid as represented in FIG. 4.

FIGS. 6 and 7 are theoretical diagrams illustrating the operation of the suction cup for obtaining the haemostasis of the tissue area onto which it is applied.

Figure 1:
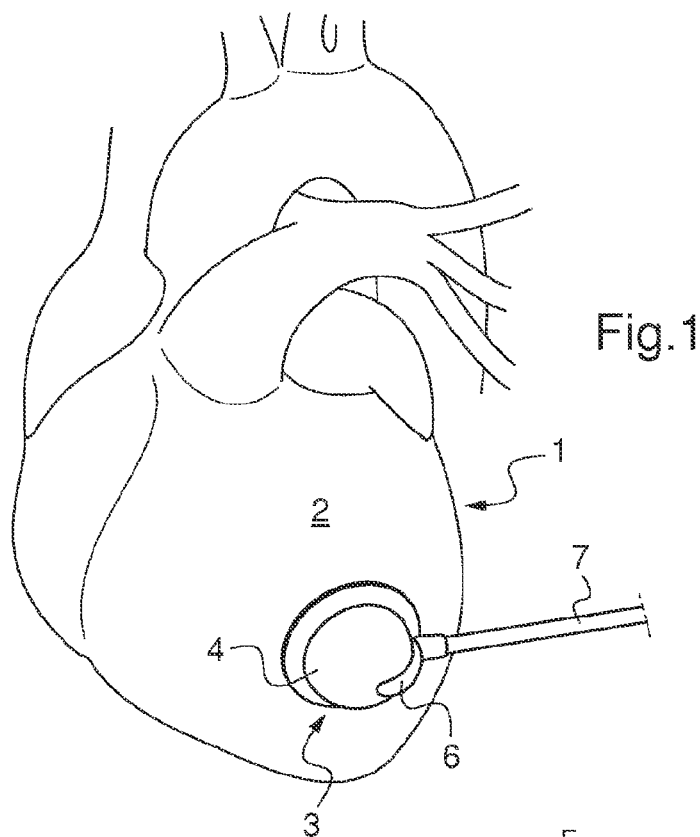
FIG. 1 is a perspective schematic view of a living organ, here a heart, with a tissue area presenting a local haemorrhage, which may be controlled through a suction cup according to the invention.

In FIG. 1, reference 1 refers to any organ, in this case a heart which is supposed to present a tissue area 2 with an important haemorrhage, which must be controlled and notably reduced, if not stopped, in order to avoid bleeding in large amounts outside and/or into the patient's thoracic cavity, wherein this may put the individual's life at risk, or, more immediately, hinder the vision and access to another area of said organ which is the object of a surgical operation.

Naturally the kind of organ which is treated is in itself indifferent to the invention, which applies generally to any haemorrhagic lesion, notably when needed for such a surgical operation or in the case of a serious wound, causing a bleeding emergency to be opposed as quickly and as efficiently as possible.

Figure 2:
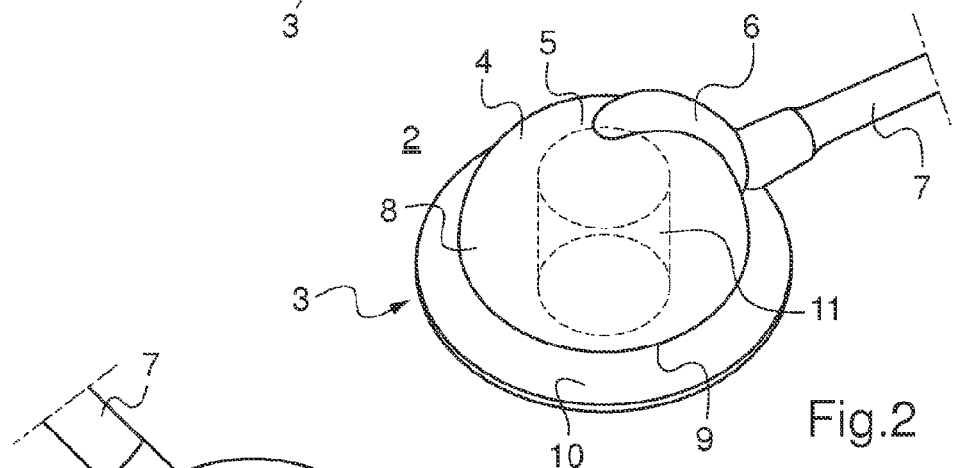
FIG. 2 is a larger scale perspective view illustrating said suction cup, as seen from above, according to a first embodiment of the invention where the inner support device is made up by a solid obturator.
Figure 3:
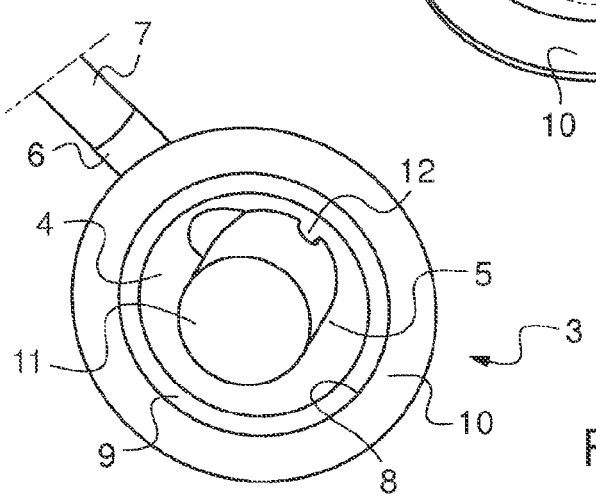
FIG. 3 represents the suction cup of FIG. 2, as seen from below.

In order to reach this aim, the invention suggests the use of an improved suction cup 3, as diagrammatically represented in FIG. 1 in the position it takes when it is placed onto the tissue area 2 where the haemorrhage takes place, and of which FIGS. 2 and 3 illustrate in greater detail the characteristic features of a first embodiment.

As may be seen in these Figures, said suction cup 3 is in the shape of an essentially hemispheric rotating dome 4, whose bottom 5, essentially at the center of its superior part, is tightly linked, through a linking device 6 which is continued by a similar linking catheter or linking tube 7, to a (not represented) external device for creating a vacuum in the inner volume 8 of the dome, once the latter is tightly applied onto the tissue area 2 through its end edge 9 as opposed to the bottom 5, wherein this edge is advantageously prolonged by a circular flange 10, which is plane and preferably sloped towards the axis of the dome, in order to present an essentially conical profile, which is flexible and able to bend slightly when the suction cup 3 is placed.

This device for creating a vacuum in the volume 8 by a suction of the air which it contains, may consist in a vacuum pump or in a Redon type suction bowl, wherein this kind of apparatus, with which one may obtain a depression of about 500-700 mm Hg, is by itself quite conventional in the art, in such a way that a detailed description thereof is not necessary here.

According to the invention and in the first embodiment which is represented, the suction cup 4 is associated, within the internal volume 8 which it defines, with an inner support device which is made up by a solid obturator 11 which appears as a straight cylinder, whose axis is the same as that of the dome, wherein said obturator is integral with the bottom 5, either as a single-piece unit with the dome, or being manufactured separately before being glued or welded against this bottom at its center.

The cylindrical obturator 11 is joined with the linking device 6 and includes at least a through hole 12 for communicating with the inner volume 8 of the dome 4 in order to let the air be pumped in and out through tube 7.

The dome 4 may be comparatively flexible, and in this case it is made of a plastic material such as a silicone resin or any other material which is biocompatible with the tissue and may be adequately sterilized before being applied onto the area 2. It may also be manufactured from a rigid material, such as a hardened epoxy resin, preferably with a silicone coating.

As for the obturator 11, it is made up of a material which is similar to that of the dome, or of a different material, with a higher rigidity. This obturator generally has, according to the axial direction of its cylinder component, a height which is essentially above that of the dome 4, in order to be able to exert on the opposite tissue area an adequate compression force when the suction cup 3 is placed, wherein this compression favours a haemostasis within this tissue, and therefore a control of the haemorrhage.

However in other cases, when this compression is not desirable nor possible, the height of the obturator 11 may be below that of the dome 4, but still sufficient to facilitate positioning of the suction cup 3 onto the tissue.

Generally the height of the dome 4, according to the various circumstances when it is used, is about 10-30 mm, and the height of the obturator may be increased or decreased by 2-5 mm. The diameter of the dome is between 5-60 mm, and on average about 50. The obturator 11 has an outside diameter which is usually about half of that of the dome 4, as measured directly above its end edge 9. The flexible circular flange 10, having a conical profile which prolongs this edge, has a width of about 3-6 mm.

In another variant of an embodiment of the invention, the inner support device of the suction cup 3 may, as illustrated in the exploded view of FIG. 4 which thus allows one to better observe the relative position of the various parts, consist in a grid 13, in the shape of a spherical segment which is coaxially assembled in the dome 4, wherein this grid, preferably made of a plastic material which is similar to that of the dome, has a plurality of holes 14, notably circular ones, as regularly distributed within its surface, these holes freely letting the air into the inner volume 8 of the suction cup while avoiding a possible clogging of the tube 7 by the various elements of waste or sediment from the tissue area 2 which is covered by the suction cup 3. In other embodiments the holes 14 of the 13 might have a different shape and be variously distributed within the surface of this grid.

Moreover, in another variant as illustrated in FIG. 5, the suction cup 3 may again use a similar perforated grid 13, but wherein the spherical segment forming this grid includes, in its peripheral edge, slightly projecting embossed contact teeth 15, which are able to grip the surface of the opposing tissue in order to better bring the suction cup to a standstill in an appropriate position on the tissue area to be covered, and then to facilitate the application of a vacuum.

FIGS. 6 and 7 illustrate the manner in which the inventive suction cup 3 allows one to carry out a quick and efficient haemostasis of a tissue area 2, which includes, as represented in FIG. 6, an open wound 16 whose lips 17 and 18, essentially facing each other, form between them a slit or an opening which is diagrammatically represented under reference 19, and through which a bleeding episode takes place, wherein this must be stopped as quickly and efficiently as possible.

The suction cup 3, which here has a solid central obturator 11 according to the first variant as described hereabove, but which could just as well be provided with a perforated inner grid as an equivalent, is applied onto the wound 16, its diameter being chosen in order for it to cover and surround the slit or opening 19 between the lips 17 and 18, the obturator 11 as supported inside the suction cup being centered and in contact with the wound, and according to its height, exerting a variable force on the wound, thus producing a slight compression on its lips.

As soon as it is in place, the suction cup 3 is linked through its linking device 6 and the catheter 7 to its outer vacuum creating device, the combination of the thus produced suction inside the suction cup (as diagrammatically represented by the arrows which appear in the Figures) and of the support brought about by the inner obturator 11, having as a result the closing of the lips 17 and 18 by reducing and finally by suppressing the slit 19 as illustrated in FIG. 7, wherein these lips progressively join each other while ensuring the quick and efficient haemostasis and healing of the wound 16, and the depression which is created under the suction cup 3 is maintained as long as necessary.

One thus obtains a suction cup with a very simple design, with a reduced manufacturing cost, and above all very efficient for quickly and effectively controlling a haemorrhagic lesion by the implementation of a haemostasis which persists in time, thus facilitating as much as possible surgical operations to be carried out on the tissue to be treated, which is where the bleeding takes place.

It is however obvious that the invention is not limited to the sole embodiments as described hereabove with reference to the appended drawings; on the contrary it includes all variants pertaining to the following claims. Notably one could contemplate assembling under a single dome in the shape of a flexible plate, covering a wider tissue area, a plurality of neighbouring obturators, provided as embossed on a second plate, being parallel to the first and tightly peripherally united with it, with piercings provided in the second plate for discharging the air which has been collected into a volume communicating with the outer suction device.

The invention claimed is:

1. A suction cup device for haemostatic control of bleeding in a tissue area during a haemorrhage or a bleeding episode, the suction cup device comprising:

a hemispheric dome having an axis of rotation and an arcuate end and a peripheral edge at distal ends of the axis of the rotation such that the arcuate end and the peripheral edge are extremities of said dome along the axis of rotation, said dome comprising a bottom part at the arcuate end, an upper part at the peripheral edge, a height defined from the upper part to the bottom part along the axis of rotation, a diameter increasing from the bottom part to the upper part along the axis of rotation, an outer surface, and an inner surface, the inner surface at the peripheral edge configured to surround and be tightly applied onto said tissue area;

a solid obturator integral with a center part of the bottom part of said dome and being shaped as a solid straight cylinder having as an axis the axis of rotation of said dome, a circumference, a solid end opposite the bottom part of the dome along the axis of said dome, and a height measured along the axis of said dome from the bottom part to the solid end of the cylinder, the obturator having a surface formed along the circumference and extending along the height of said obturator and the solid end, the height of said obturator being less than the height of said dome, the solid end being closer to the peripheral edge of the dome than the bottom part of the dome, the solid end being sufficiently close to the peripheral edge of said dome such that when the peripheral edge is positioned onto said tissue area having an open wound with lips forming edges of the wound and suction is applied to create a vacuum in the inner volume, the solid end exerts a compression force onto the lips so that the lips join together and maintain said tissue area in place at the upper part of said dome so as to allow haemostasis to be carried out on the tissue area;

an inner volume delimited by the surface of the obturator and the inner surface of the dome from the obturator at the center part of the bottom part of the dome to the upper part at the peripheral edge, said inner volume being empty;

a linking device positioned at the bottom part of said dome, said linking device configured to tightly link the inner volume of said dome to a catheter or a linking tube of an outer suction and vacuum creating device so that suction can be applied in the inner volume of said dome when the peripheral edge of the dome is positioned on said tissue area, to provide a depression in pressure in the inner volume surrounding the tissue area; and a through hole linking the inner volume of the dome between the inner surface and the solid obturator to said linking device, said through hole being located at (i) the bottom part of said dome proximate to the obturator and/or (ii) along the height of the cylinder of said solid obturator proximate to where the cylinder contacts the bottom part of said dome.

2. The suction cup device according to claim 1, wherein the solid obturator comprises said through hole.

3. The suction cup device according to claim 1, wherein the dome and the solid obturator form a single-piece unit.

4. The suction cup device according to claim 1, wherein the dome and the solid obturator are glued together at the bottom part of the dome.

5. The suction cup device according to claim 1, wherein the solid obturator has a diameter that is about half of the diameter of the inner surface at the peripheral edge of the dome.

6. The suction cup device according to claim 1, wherein the dome includes a plane circular supporting flange, said flange having a conical profile sloped towards the axis of said dome and prolonging the peripheral edge of said dome, and said flange being configured to contact with the tissue area which it surrounds.

7. The suction cup device according to claim 6, wherein the plane circular supporting flange has a tapered shape having the same axis as the axis of rotation of the dome.

8. The suction cup device according to claim 1, wherein the dome is flexible and formed in a silicone resin material or analogous, which is biocompatible with the tissue area to be treated.

9. The suction cup device according to claim 1, wherein the peripheral edge of the dome has a diameter when applied onto the tissue area that is between 5-60 mm.

10. The suction cup device according to claim 1, wherein the height of the suction cup is between 10-30 mm.

11. The suction cup device according to claim 1, further comprising an outer vacuum-creating device, wherein said outer vacuum-creating device is a vacuum pump or a suction bowl.

12. The suction cup device according to claim 11, wherein the outer vacuum-creating device is configured to create in suction a depression between 500-700 mm Hg.

13. A suction cup device for haemostatic control of bleeding in a tissue area during a haemorrhage or a bleeding episode, the suction cup device consisting of:
a hemispheric dome having an axis of rotation, an arcuate end at one end of the axis of rotation, the arcuate end being a bottom part of said dome, a peripheral edge at another end of the axis of rotation, the peripheral edge being an upper part of said dome, a height defined from the upper part to the bottom part along the axis of rotation, a diameter increasing from the bottom part to the upper part along the height of said dome, an outer surface, and an inner surface;
a solid obturator being integral with a center part of the bottom part of said dome, said solid obturator having a perimeter, a height extending from the bottom part towards the peripheral edge, the height of said solid obturator being less than the height of said dome, a solid contact surface at the height of said solid obturator, the solid contact surface being closer to the peripheral edge than the bottom part, and a lateral surface along the perimeter and extending the height of said solid obturator;
an inner volume contained within the dome and delimited by the inner surface of the dome from the peripheral edge to the obturator at the center part of the bottom part of the dome, the lateral surface of the obturator and the solid end surface of the obturator;
a through-hole being located (i) at the bottom part of said dome proximate to where said solid obturator is integral with the dome and/or (ii) on the perimeter of said solid obturator at a location proximate to where said solid obturator is integral with the dome;
a linking device positioned at the outer surface of said dome, said linking device configured to tightly link the through hole to a catheter or a linking tube of an outer suction and vacuum creating device so suction may be applied to the inner volume of said dome via the through hole and create a vacuum in the inner volume,
wherein the solid contact surface is sufficiently close to the peripheral edge such that when the peripheral edge is positioned onto said tissue area having an open wound with lips forming edges around the wound and suction is applied via said through hole to create said vacuum in the inner volume, the solid contact surface exerts a compression force onto the lips to join the lips together and maintain said tissue area in place at the upper part of said dome during said suction so as to allow haemostasis to be carried out on the tissue area.

* * * * *